(12) United States Patent
Childers et al.

(10) Patent No.: US 8,221,529 B2
(45) Date of Patent: *Jul. 17, 2012

(54) DIALYSIS SYSTEMS AND METHODS INCLUDING CASSETTE WITH AIR REMOVAL

(75) Inventors: Robert W. Childers, Trinity, FL (US);
Donald D. Busby, Tampa, FL (US);
Michael E. Hogard, Odessa, FL (US);
Michael R. Prisco, Geneva, IL (US);
Atif M. Yardimci, Vernon Hills, IL (US); James C. Laird, Grayslake, IL (US)

(73) Assignees: Baxter International, Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/301,306

(22) Filed: Nov. 21, 2011

(65) Prior Publication Data

US 2012/0065581 A1   Mar. 15, 2012

Related U.S. Application Data

(60) Continuation of application No. 13/030,855, filed on Feb. 18, 2011, now Pat. No. 8,080,091, which is a division of application No. 11/865,583, filed on Oct. 1, 2007, now Pat. No. 7,892,331.

(51) Int. Cl.
*B01D 19/00* (2006.01)

(52) U.S. Cl. .............. 95/260; 96/215; 96/207; 96/189

(58) Field of Classification Search .................... 95/262, 95/260; 96/204, 220, 215, 207, 189; 604/5.04
See application file for complete search history.

(56) References Cited

U.S. PATENT DOCUMENTS

| 250,868 A | 12/1881 | Abbott |
| 927,476 A | 7/1909 | Barker |
| 1,505,050 A | 8/1924 | Lauritsen |
| 2,292,007 A | 8/1942 | Morgan |
| 3,044,236 A | 7/1962 | Bearden et al. |
| 3,074,645 A | 1/1963 | Main |
| 3,095,062 A | 6/1963 | Neely |
| 3,229,445 A | 1/1966 | Kraft |
| 3,287,885 A | 11/1966 | Sommer |

(Continued)

FOREIGN PATENT DOCUMENTS

CH   296007   1/1954

(Continued)

*Primary Examiner* — Duane Smith
*Assistant Examiner* — Douglas Theisen
(74) *Attorney, Agent, or Firm* — K&L Gates LLP

(57) ABSTRACT

In an embodiment, a dialysis fluid cassette is disclosed. The cassette includes a plurality of walls defining at least one valve chamber, a dialysis fluid inlet, a dialysis fluid outlet and a dialysis fluid pathway. The cassette further includes a baffle extending from a first one of the walls to an opposing second one of the walls. The baffle includes an end fixed to a third one of the plurality of walls and a free end. The fixed end separates the dialysis fluid inlet from the dialysis fluid outlet and the baffle and the plurality of walls are constructed and arranged such that the flow of dialysis fluid along the pathway defined in part by the baffle slows as the flow approaches the free end of the baffle.

15 Claims, 10 Drawing Sheets

U.S. PATENT DOCUMENTS

| | | | |
|---|---|---|---|
| 3,295,297 A | 1/1967 | Collins |
| 3,342,019 A | 9/1967 | Smythe |
| 3,412,760 A | 11/1968 | Franck |
| 3,527,572 A | 9/1970 | Urkiewicz |
| 3,581,464 A | 6/1971 | Bhuta et al. |
| 3,598,727 A | 8/1971 | Wilock |
| 3,677,710 A | 7/1972 | Hirsch |
| 3,744,492 A | 7/1973 | Leibinsohn |
| 3,769,207 A | 10/1973 | Baer |
| 3,771,288 A | 11/1973 | Wisman et al. |
| 3,795,088 A | 3/1974 | Esmond |
| 3,827,561 A | 8/1974 | Serfass et al. |
| 3,834,386 A | 9/1974 | Sisley |
| 3,849,071 A | 11/1974 | Kayser |
| 3,908,653 A | 9/1975 | Kettering |
| 3,964,479 A | 6/1976 | Boag et al. |
| 3,976,311 A | 8/1976 | Spendlove |
| 3,985,134 A | 10/1976 | Lissot et al. |
| 3,996,027 A | 12/1976 | Schnell et al. |
| 4,031,891 A | 6/1977 | Jess |
| 4,038,190 A | 7/1977 | Baudet et al. |
| 4,047,563 A | 9/1977 | Kurata |
| 4,048,995 A | 9/1977 | Mittleman |
| 4,054,522 A | 10/1977 | Pinkerton |
| 4,061,031 A | 12/1977 | Grimsrud |
| 4,102,655 A | 7/1978 | Jeffery et al. |
| 4,137,160 A | 1/1979 | Ebling et al. |
| 4,149,860 A | 4/1979 | Kulik |
| 4,151,088 A | 4/1979 | Wolf, Jr. et al. |
| 4,191,182 A | 3/1980 | Popovich et al. |
| 4,200,095 A | 4/1980 | Reti |
| 4,293,413 A | 10/1981 | Schnell |
| 4,304,670 A | 12/1981 | Watanabe et al. |
| 4,311,137 A | 1/1982 | Gerard |
| 4,325,715 A | 4/1982 | Bowman et al. |
| 4,344,777 A | 8/1982 | Siposs |
| 4,345,919 A | 8/1982 | Wilkinson et al. |
| 4,345,999 A | 8/1982 | Sigdell et al. |
| 4,353,368 A | 10/1982 | Slovak et al. |
| 4,363,641 A | 12/1982 | Finn, III |
| 4,368,118 A | 1/1983 | Siposs |
| 4,424,068 A | 1/1984 | McMillan |
| 4,427,009 A | 1/1984 | Wells et al. |
| 4,433,971 A | 2/1984 | Lindsay et al. |
| 4,486,188 A | 12/1984 | Altshuler et al. |
| 4,493,705 A | 1/1985 | Gordon et al. |
| 4,512,163 A | 4/1985 | Wells et al. |
| 4,531,937 A | 7/1985 | Yates |
| 4,568,333 A | 2/1986 | Sawyer et al. |
| 4,583,981 A | 4/1986 | Urquhart et al. |
| 4,586,925 A | 5/1986 | Carlsson et al. |
| 4,622,032 A | 11/1986 | Katsura et al. |
| 4,643,713 A | 2/1987 | Viitala |
| 4,643,715 A | 2/1987 | Isono et al. |
| 4,666,598 A | 5/1987 | Heath et al. |
| 4,681,606 A | 7/1987 | Swan, Jr. et al. |
| 4,722,725 A | 2/1988 | Sawyer et al. |
| 4,722,731 A | 2/1988 | Vailancourt |
| 4,734,269 A | 3/1988 | Clarke et al. |
| 4,806,135 A | 2/1989 | Siposs |
| 4,932,987 A | 6/1990 | Molina |
| 4,941,875 A | 7/1990 | Brennan |
| 4,946,439 A | 8/1990 | Eggers |
| 311,061 | 10/1990 | Vrana et al. |
| 4,976,685 A | 12/1990 | Block, Jr. |
| 4,997,464 A | 3/1991 | Kopf |
| 5,047,147 A | 9/1991 | Chevallet et al. |
| 5,049,492 A | 9/1991 | Sauer et al. |
| 5,059,173 A | 10/1991 | Sacco |
| 5,061,236 A | 10/1991 | Sutherland et al. |
| 5,061,365 A | 10/1991 | Utterberg |
| 5,112,480 A | 5/1992 | Hukasawa |
| 5,167,921 A | 12/1992 | Gordon |
| 5,178,763 A | 1/1993 | Delaunay |
| 5,204,000 A | 4/1993 | Steadman et al. |
| 5,228,889 A | 7/1993 | Cortial et al. |
| 5,246,560 A | 9/1993 | Nekoksa et al. |
| 5,268,077 A | 12/1993 | Bubik et al. |
| 5,328,461 A | 7/1994 | Utterberg |
| 5,356,376 A | 10/1994 | Milijasevic et al. |
| 5,358,481 A | 10/1994 | Todd et al. |
| 5,368,555 A | 11/1994 | Sussman et al. |
| 5,394,732 A | 3/1995 | Johnson et al. |
| 5,411,705 A | 5/1995 | Thor et al. |
| 5,421,815 A | 6/1995 | Noguchi et al. |
| 5,429,595 A | 7/1995 | Wright, Jr. et al. |
| 5,441,636 A | 8/1995 | Chevallet et al. |
| 5,468,388 A | 11/1995 | Goddard et al. |
| 5,489,385 A | 2/1996 | Raabe et al. |
| 5,503,801 A | 4/1996 | Brugger |
| 5,509,895 A | 4/1996 | Noguchi et al. |
| 5,520,640 A | 5/1996 | Utterberg |
| 5,578,070 A | 11/1996 | Utterberg |
| 5,591,251 A | 1/1997 | Brugger |
| 5,605,540 A | 2/1997 | Utterberg |
| 5,637,081 A | 6/1997 | Noguchi et al. |
| 5,643,205 A | 7/1997 | Utterberg |
| 5,650,071 A | 7/1997 | Brugger et al. |
| 5,674,199 A | 10/1997 | Brugger |
| 5,681,294 A | 10/1997 | Osborne et al. |
| 5,683,355 A | 11/1997 | Fini et al. |
| 5,730,730 A | 3/1998 | Darling, Jr. |
| 5,763,266 A | 6/1998 | Palsson et al. |
| 5,776,091 A | 7/1998 | Brugger et al. |
| 5,800,597 A | 9/1998 | Perrotta et al. |
| 5,830,185 A | 11/1998 | Block, Jr. |
| 5,849,065 A | 12/1998 | Wojke |
| 5,851,202 A | 12/1998 | Carlsson |
| 5,858,239 A | 1/1999 | Kenley et al. |
| 5,863,421 A | 1/1999 | Peter, Jr. et al. |
| 5,895,368 A | 4/1999 | Utterberg |
| 5,928,889 A | 7/1999 | Bakich et al. |
| 5,931,990 A | 8/1999 | Andrews |
| 5,951,870 A | 9/1999 | Utterberg |
| 5,980,741 A | 11/1999 | Schnell et al. |
| 5,983,947 A | 11/1999 | Utterberg |
| 5,989,318 A | 11/1999 | Schroll |
| 6,010,623 A | 1/2000 | Schnell et al. |
| 6,019,824 A | 2/2000 | Schnell |
| 6,046,806 A | 4/2000 | Thompson |
| 6,051,134 A | 4/2000 | Schnell et al. |
| 6,053,967 A | 4/2000 | Heilmann et al. |
| 6,066,111 A | 5/2000 | Brockhoff |
| 6,071,269 A | 6/2000 | Schnell et al. |
| 6,117,342 A | 9/2000 | Schnell et al. |
| 6,171,484 B1 | 1/2001 | Schnell et al. |
| 6,176,903 B1 | 1/2001 | Wamsiedler |
| 6,187,198 B1 | 2/2001 | Utterberg |
| 6,206,954 B1 | 3/2001 | Schnell et al. |
| 6,251,167 B1 | 6/2001 | Berson |
| 6,312,414 B1 | 11/2001 | Brockhoff et al. |
| 6,344,139 B1 | 2/2002 | Utterberg |
| 6,357,600 B1 | 3/2002 | Scagliarini |
| 6,391,541 B1 | 5/2002 | Petersen et al. |
| 6,391,638 B1 | 5/2002 | Shaaltiel |
| 6,464,878 B2 | 10/2002 | Utterberg |
| 6,481,455 B2 | 11/2002 | Gustafson et al. |
| 6,514,255 B1 | 2/2003 | Ferree |
| 6,537,356 B1 | 3/2003 | Soriano |
| 6,562,107 B2 | 5/2003 | Purdom et al. |
| 6,755,801 B2 | 6/2004 | Utterberg et al. |
| 6,827,862 B1 | 12/2004 | Brockhoff et al. |
| 7,892,331 B2 * | 2/2011 | Childers et al. ............ 96/189 |
| 2001/0042441 A1 | 11/2001 | Purdom et al. |
| 2004/0019313 A1 | 1/2004 | Childers et al. |

FOREIGN PATENT DOCUMENTS

| | | |
|---|---|---|
| DE | 1806654 | 5/1970 |
| EP | 0 058 325 | 8/1982 |
| EP | 0 106 026 | 4/1984 |
| EP | 0 143 340 | 6/1985 |
| EP | 0 318 993 | 6/1989 |
| EP | 0 350 675 | 1/1990 |
| EP | 0 501 144 | 1/1992 |
| EP | 0 587 251 | 3/1994 |
| EP | 0 776 222 | 4/2003 |
| GB | 1 408 319 | 10/1975 |

| | | |
|---|---|---|
| GB | 1 554 810 | 10/1979 |
| GB | 2 061 755 | 5/1981 |
| GB | 2 212 739 | 8/1989 |
| WO | 98/23353 | 6/1998 |
| WO | WO 9823353 * | 6/1998 |
| WO | 2005/089832 | 9/2005 |
| WO | 2006/120415 | 11/2006 |
| WO | WO 2006120415 A1 * | 11/2006 |

* cited by examiner

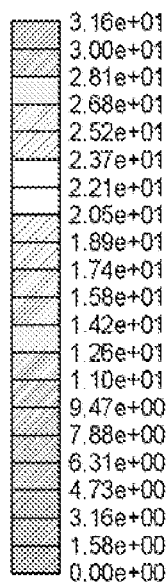
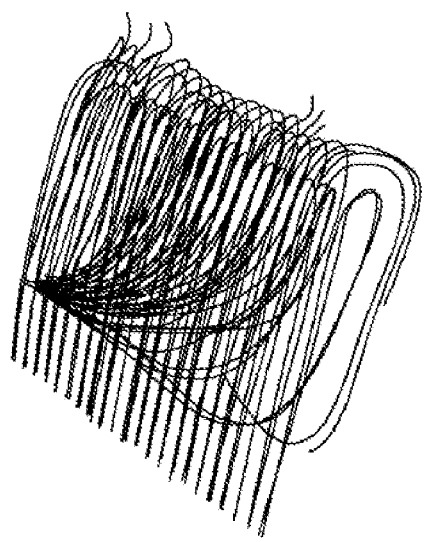
FIG. 6
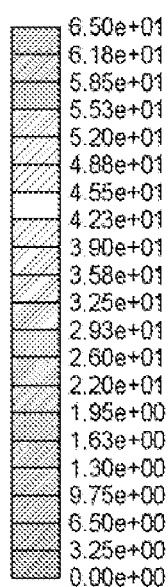
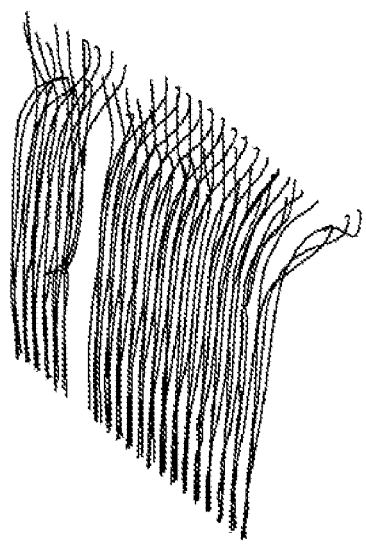
FIG. 7

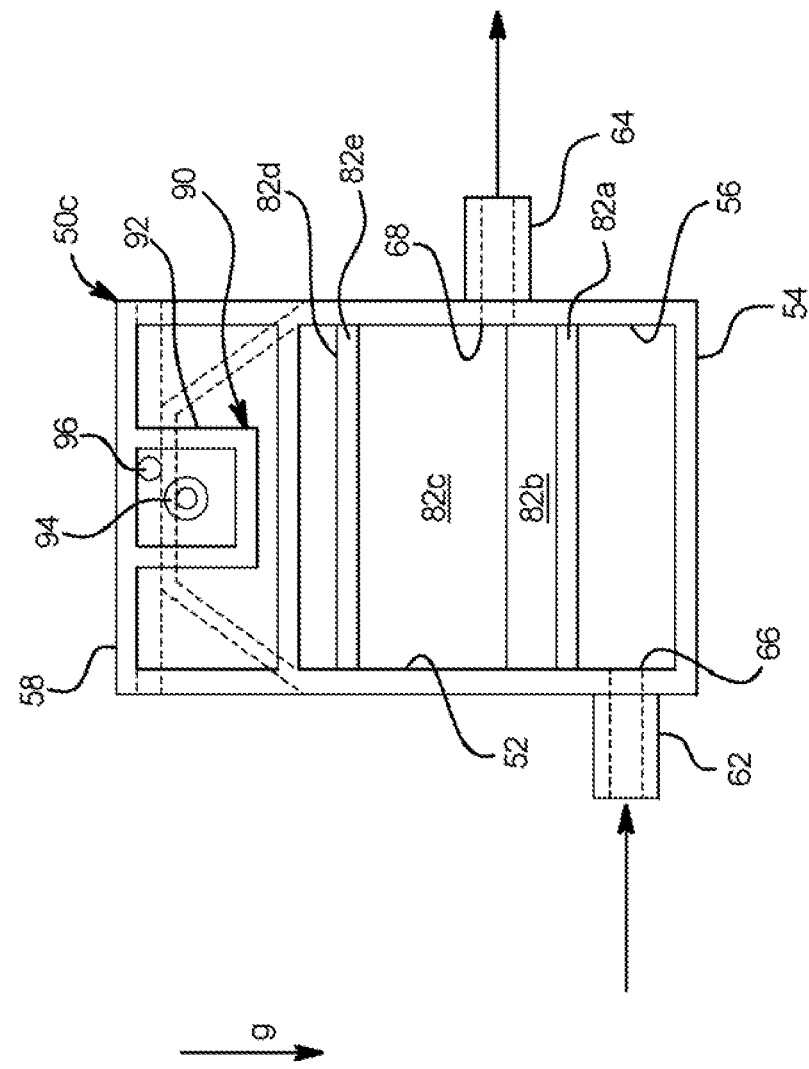
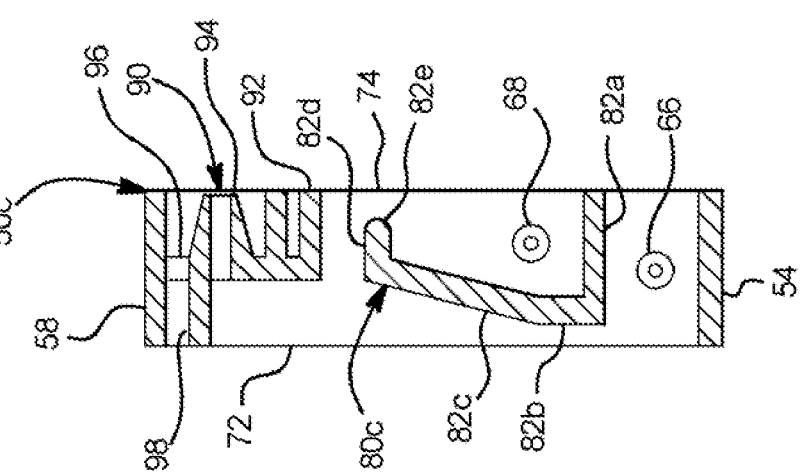

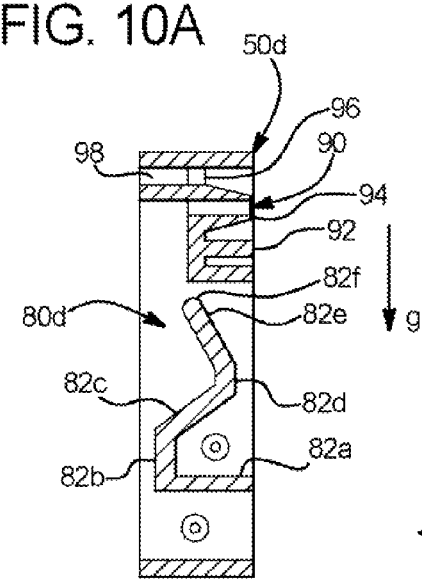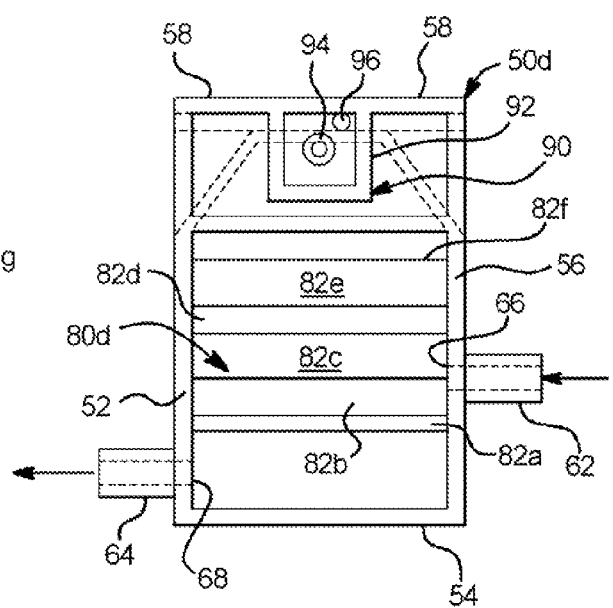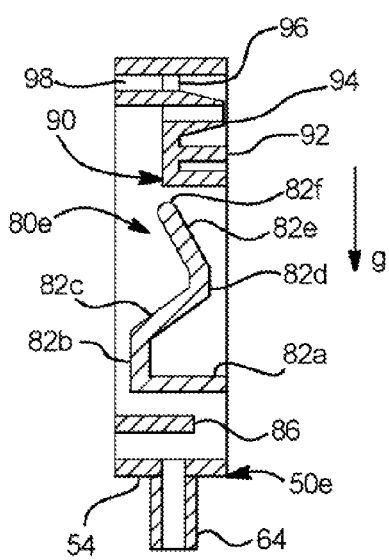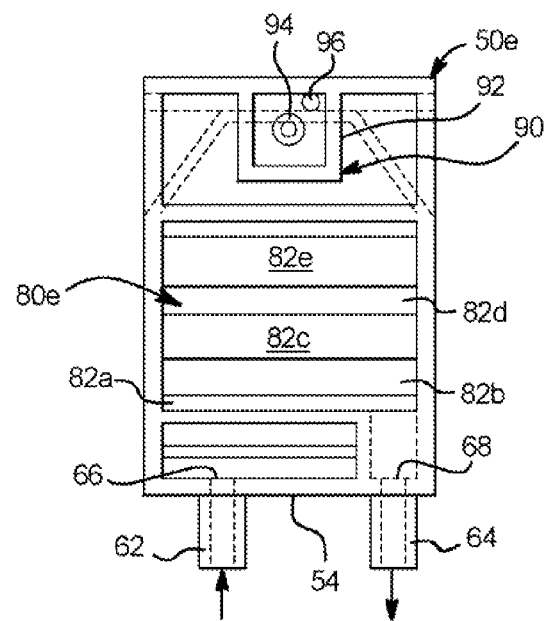

DIALYSIS SYSTEMS AND METHODS INCLUDING CASSETTE WITH AIR REMOVAL

PRIORITY

This application claims priority to and the benefit as a continuation of U.S. patent application entitled, "Dialysis Systems and Methods Including Cassette With Fluid Heating And Air Removal", Ser. No. 13/030,855, filed Feb. 18, 2011 which is a divisional of U.S. patent application entitled, "Dialysis Systems Having Air Separation Chambers With Internal Structures To Enhance Air Removal", Ser. No. 11/865,583, filed Oct. 1, 2007, the entire contents of each of which are incorporated herein by reference and relied upon.

BACKGROUND

The examples discussed below relate generally to medical fluid delivery. More particularly, the examples disclose systems, methods and apparatuses for dialysis such as hemodialysis ("HD") automated peritoneal dialysis ("APD").

Due to various causes, a person's renal system can fail. Renal failure produces several physiological derangements. It is no longer possible to balance water and minerals or to excrete daily metabolic load. Toxic end products of nitrogen metabolism (urea, creatinine, uric acid, and others) can accumulate in blood and tissue.

Kidney failure and reduced kidney function have been treated with dialysis. Dialysis removes waste, toxins and excess water from the body that normal functioning kidneys would otherwise remove. Dialysis treatment for replacement of kidney functions is critical to many people because the treatment is life saving.

One type of kidney failure therapy is Hemodialysis ("HD"), which in general uses diffusion to remove waste products from a patient's blood. A diffusive gradient occurs across the semi-permeable dialyzer between the blood and an electrolyte solution called dialysate to cause diffusion. Hemofiltration ("HF") is an alternative renal replacement therapy that relies on a convective transport of toxins from the patient's blood. This therapy is accomplished by adding substitution or replacement fluid to the extracorporeal circuit during treatment (typically ten to ninety liters of such fluid). That substitution fluid and the fluid accumulated by the patient in between treatments is ultrafiltered over the course of the HF treatment, providing a convective transport mechanism that is particularly beneficial in removing middle and large molecules (in hemodialysis there is a small amount of waste removed along with the fluid gained between dialysis sessions, however, the solute drag from the removal of that ultrafiltrate is not enough to provide convective clearance).

Hemodiafiltration ("HDF") is a treatment modality that combines convective and diffusive clearances. HDF uses dialysate flowing through a dialyzer, similar to standard hemodialysis, to provide diffusive clearance. In addition, substitution solution is provided directly to the extracorporeal circuit, providing convective clearance.

Most HD (HF, HDF) treatments occur in centers. A trend towards home hemodialysis ("HHD") exists today in part because HHD can be performed daily, offering therapeutic benefits over in-center hemodialysis treatments, which occur typically bi- or tri-weekly. Studies have shown that a patient receiving more frequent treatments removes more toxins and waste products than a patient receiving less frequent but perhaps longer treatments. A patient receiving more frequent treatments does not experience as much of a down cycle as does an in-center patient who has built-up two or three days worth of toxins prior to a treatment. In certain areas, the closest dialysis center can be many miles from the patient's home causing door-to-door treatment time to consume a large portion of the day. HHD can take place overnight or during the day while the patient relaxes, works or is otherwise productive.

Another type of kidney failure therapy is peritoneal dialysis, which infuses a dialysis solution, also called dialysate, into a patient's peritoneal cavity via a catheter. The dialysate contacts the peritoneal membrane of the peritoneal cavity. Waste, toxins and excess water pass from the patient's bloodstream, through the peritoneal membrane and into the dialysate due to diffusion and osmosis, i.e., an osmotic gradient occurs across the membrane. Osmotic agent in dialysis provides the osmotic gradient. The spent dialysate is drained from the patient, removing waste, toxins and excess water from the patient. This cycle is repeated.

There are various types of peritoneal dialysis therapies, including continuous ambulatory peritoneal dialysis ("CAPD"), automated peritoneal dialysis ("APD"), tidal flow dialysate and continuous flow peritoneal dialysis ("CFPD"). CAPD is a manual dialysis treatment. Here, the patient manually connects an implanted catheter to a drain to allow spent dialysate fluid to drain from the peritoneal cavity. The patient then connects the catheter to a bag of fresh dialysate to infuse fresh dialysate through the catheter and into the patient. The patient disconnects the catheter from the fresh dialysate bag and allows the dialysate to dwell within the peritoneal cavity, wherein the transfer of waste, toxins and excess water takes place. After a dwell period, the patient repeats the manual dialysis procedure, for example, four times per day, each treatment lasting about an hour. Manual peritoneal dialysis requires a significant amount of time and effort from the patient, leaving ample room for improvement.

Automated peritoneal dialysis ("APD") is similar to CAPD in that the dialysis treatment includes drain, fill and dwell cycles. APD machines, however, perform the cycles automatically, typically while the patient sleeps. APD machines free patients from having to manually perform the treatment cycles and from having to transport supplies during the day. APD machines connect fluidly to an implanted catheter, to a source or bag of fresh dialysate and to a fluid drain. APD machines pump fresh dialysate from a dialysate source, through the catheter and into the patient's peritoneal cavity. APD machines also allow for the dialysate to dwell within the cavity and for the transfer of waste, toxins and excess water to take place. The source can include multiple sterile dialysate solution bags.

APD machines pump spent dialysate from the peritoneal cavity, though the catheter, and to the drain. As with the manual process, several drain, fill and dwell cycles occur during dialysis. A "last fill" occurs at the end of APD and remains in the peritoneal cavity of the patient until the next treatment.

In any of the above modalities, entrained air and other gases are a concern. Entrained air can cause inaccuracies when pumping dialysate for either PD or HD. Entrained air can cause a reduction in effective surface area in a hemodialysis filter when it accumulates on the filter fibers, leading to a reduction in effectiveness of the therapy. Entrained air entering a patient's peritoneum during PD can cause discomfort. Entrained air entering a patient's bloodstream during HD can have severe consequences. Accordingly, a need exists to provide an apparatus that ensures that entrained air is removed from dialysate or blood prior to delivering such fluids to the patient.

SUMMARY

The present disclosure relates to air and gas removal for dialysis systems and extracorporeal devices, e.g., blood separation, blood warming, etc. The structures disclosed herein can be performed in any type of peritoneal dialysis treatment or blood dialysis treatment such as hemodialysis, hemofiltration, hemodiafiltration and continuous renal replacement therapy. The embodiments below are disclosed in connection with a dialysis cassette that is loaded into a dialysis instrument. The dialysis cassette is part of an overall dialysis set which can include one or more supply bag, or connection to the dialysate generation system, one or more drain bag, a heater bag and associated tubing connecting the bags to the dialysis cassette. The user places the dialysis cassette within the dialysis instrument for therapy. The dialysis cassette can include one or more pump chamber, flow path and/or valve chamber. The dialysis instrument includes one or more pump actuator that actuates the pump chamber of the disposable cassette. The dialysis instrument also includes one or more valve actuator that actuates the valve chamber of the disposable cassette. The disposable cassette can also include a fluid heating pathway that operates with a fluid heater of the dialysis instrument. The disposable cassette can also include various regions for sensing pressure, fluid composition, fluid temperature, and fluid levels.

While air traps 50 are shown herein in connection with a disposable set described below, the separation chambers are alternatively stand-alone apparatuses that operate independent of the disposable cassette. Further, the present disclosure mainly discusses air but other gases can also be present and therefore the present air separation chambers can also trap these gases. In PD for example, gases from the patient can become entrained in fluid being pumped form the system. Also, gases from dialysate concentrate, such as bicarbonate can become entrained in fresh dialysate. It is expressly contemplated for the air separation chambers of the present disclosure to remove these additional types of gases.

As mentioned above, air in dialysate or dialysis fluid as well as air in blood needs to be removed before any of these fluids are either delivered to a dialyzer or patient. Air can be present in the system via air trapped in supply bags, air trapped in the tubes leading from the supply bags to the disposable cassette, air not completely primed from the disposable cassette itself and air that is released from solution when the dialysis fluid is mixed and/or heated. Air can also signal a leak in the disposable unit.

The air traps discussed below are shown generally in connection with a dialysis fluid, such as dialysate, having entrained air. It should be appreciated however that the embodiments are applicable equally to the removal of air from blood pumped from a patient to a hemodialyzer or hemofilter. As used herein, the term dialysis fluid includes, without limitation, mixed dialysate, mixed infusate, mixed replacement fluid, concentrated components of any of these, and blood.

In one embodiment, the disposable cassette defines an air separation chamber that has a fluid inlet and a fluid outlet. An inlet valve and an outlet valve are paired with the fluid inlet and fluid outlet of the air separation chamber, respectively. The air separation chamber also includes an air vent outlet, which is in fluid communication with one or more air vent valve. The air removed from fluid in the air trap is sent to atmosphere, to a holding vessel such as an empty bag or a fluid filled bag (e.g., saline bag or dialysate bag), or to a drain, for example, whichever is desired.

In one embodiment, the air separation chamber is configured with respect to the other components of the disposable cassette such that when the cassette is loaded into the dialysis instrument, the fluid inlet and fluid outlet are located towards a bottom or bottom wall of the air separation chamber, while the air outlet is located at or near the top of the dialysis instrument. Such configuration allows buoyancy forces to lift air bubbles from the dialysis fluid to the top of the air separation chamber for venting.

The dialysis cassette in one embodiment includes a rigid portion, which can be a hard plastic. The rigid portion is formed to have pump chambers (e.g., for diaphragm pumps) or pump tubing (for peristaltic pumping), fluid pathways and valve chambers. The rigid portion also defines some or all of the air separation chamber. It is contemplated that the disposable cassette will have flexible sheeting welded to one or both sides of the rigid portion of the cassette. The flexible sheeting allows a pneumatic or mechanical force to be applied to the pump chambers (e.g., diaphragm) and valve chambers to operate those chambers. It is also contemplated that at least one outer surface of the air separation chamber consumes a portion of one or both flexible sheets. In addition, one or both sides of the dialysis cassette can be rigid.

The disposable cassette can have a base wall or mid-plane that divides the disposable cassette into first and second sides. For example, in one embodiment the flow paths are provided on one side of the disposable cassette (one side of the base wall), while the pump and valve chambers are provided on the other side of the disposable cassette. In one embodiment, the mid-plane is not present within the air separation chamber. The air separation chamber can be bonded on two sides by flexible sheeting. Alternatively, the mid-plane is not provided in the air separation chamber, however, the outer walls of the air separation chamber are rigid and adhere to the top, bottom, inlet and outlet walls via a suitable sealing process. Further alternatively, one outer wall is rigid, while the other outer wall is flexible sheeting.

The air separation chamber includes one or more baffle or separation wall that is configured to disrupt the flow of fluid through the air separation chamber, promoting the separation of air from the dialysis fluid. In one embodiment, the baffle or separation wall extends horizontally to separate a dialysis fluid inlet from a dialysis fluid outlet. The inlet and outlet here are formed in an internal side wall formed by the rigid portion of the cassette. The inlet and outlet can be formed in the same internal side wall or in different internal side walls. The inlet can be provided below the outlet or vice versa. The inlet and outlet are alternatively vertically disposed with respect to the air separation chamber. In one embodiment, the baffle or separation wall extends from one internal side wall to the other internal side wall, forcing the dialysis fluid over the free or distal end of the baffle.

The baffle or separation wall extends vertically up the air separation chamber, ending at a free end at which the dialysis fluid flows over and down towards the dialysis fluid outlet located on the opposite side of the baffle or separation wall. The baffle accordingly forces the dialysis fluid to make an inverted-U-like flow path.

The inlet or "filling" side of the baffle or separation wall in one embodiment is angled or tapered inwardly towards a center of the air separation chamber. This feature serves a number of purposes. First, the angle or taper causes the cross-sectional area of the dialysis fluid flow to increase as it rises up the inlet side of the baffle so that the fluid flow velocity decreases. The slowing of the dialysis fluid velocity also reduces the velocity of the air bubbles that are traveling with the fluid. When the fluid flow direction changes from vertically upward to horizontal and then vertically downward, as it is directed towards the exit on the opposite side of the separation wall, the buoyancy forces are able to overcome the drag exerted on the air bubbles by the increasingly slower moving fluid flow. The air bubbles can then float into the collection portion at the top of the air trap.

Second, the horizontal flow section at the top of the vertical wall has no downward velocity component so the air bubbles are momentarily free to float up into the air collection portion at the top of the air trap. As the fluid direction changes from horizontal to vertically down, the air bubbles continue to be separated from the flow of the dialysis solution as it turns downward and flows toward the outlet. The vertically oriented air separation wall can have multiple tapers or bends as desired. It can also have flow directors that spread the flow uniformly along the vertically oriented separation wall.

In one embodiment, the horizontal flow section at the top of vertical wall is lengthened by a horizontally disposed baffle, or separation wall. This further enhances the air separation since the air bubbles are not acted upon by a downward drag force for a longer period of time. The horizontal section can slope slightly upward so that the air bubbles have both a buoyancy force and a velocity force to counter the drag produced by the fluid when it begins to flow vertically downward.

The second separation wall can be provided alternatively fluidly ahead or upstream of the first, e.g., tapered, baffle to provide a series or combination of dialysis fluid direction changes, for example, to provide a serpentine flow path. Here, the inlet and outlet can be disposed vertically with respect to the air separation chamber when mounted, to accommodate the provision of the baffle walls in series between the dialysis fluid inlet and dialysis fluid outlet.

The dialysis fluid cassette in one embodiment includes valve chambers that communicate fluidly with the fluid inlet, the fluid outlet and an air outlet of the air separation chamber. The valve chambers can be located directly adjacent to the air separation chamber or further upstream or downstream from the air separation chamber. In one alternative embodiment, the air vent valve chamber (and port) are located within the air separation chamber. Here, at least one outer surface of the air separation chamber (covering the valve chamber port) is made of flexible cassette sheeting.

In one alternative embodiment, the air separation chamber includes concentric tubes. The outer tube for example includes a dialysis fluid inlet. The inner tube extends a certain distance within the outer tube and is a dialysis fluid outlet. Dialysis fluid entering the concentric tube air separation chamber flows vertically up along the inside of the outer tube and the outside of the inner tube before rising above the inner tube. The dialysis fluid then spills into the inner tube and flows downwardly out the bottom and the outlet of the tube.

The concentric tubes provide a relatively large cross-sectional area for the dialysis fluid to slowly flow up the outside of the inner tube, allowing buoyancy forces time to dislodge the gas bubbles from the dialysis fluid. The concentric tube air separation chamber can be made part of the disposable cassette, be connected to the disposable or be separate from but in fluid communication with the disposable cassette.

In a further alternative embodiment, the disposable cassette provides a fluid heating area that is large enough to function additionally as an air separation chamber. In certain figures illustrated below, the disposable cassette includes a cylindrical fluid heating area. The fluid heating/air separation inlet can be located above or below the fluid heating/air separation outlet. In either case, a vent opening is located elevationally above both the inlet and outlet when the cassette is mounted within the dialysis instrument. This configuration is advantageous in one respect because gas bubbles tend to come free from the dialysis fluid when the fluid is heated.

It is accordingly an advantage of the present disclosure to provide improved air separation chambers for the removal of air from the dialysis fluid or from blood flowing through a disposable dialysis fluid apparatus.

Additional features and advantages are described herein, and will be apparent from, the following Detailed Description and the figures.

BRIEF DESCRIPTION OF THE FIGURES

FIGS. 6 to 8 show computer simulations of the operation of the air separation chamber of FIG. 5.

FIGS. 9A and 9B are sectioned elevation and rear elevation views, respectfully, of one alternative embodiment for an air separation chamber of the present disclosure.

FIGS. 10A and 10B are sectioned elevation and rear elevation views, respectfully, of a another alternative embodiment for an air separation chamber of the present disclosure.

FIGS. 11A and 11B are sectioned elevation and rear elevation views, respectfully, of a further alternative embodiment for an air separation chamber of the present disclosure.

DETAILED DESCRIPTION

Figure 1:
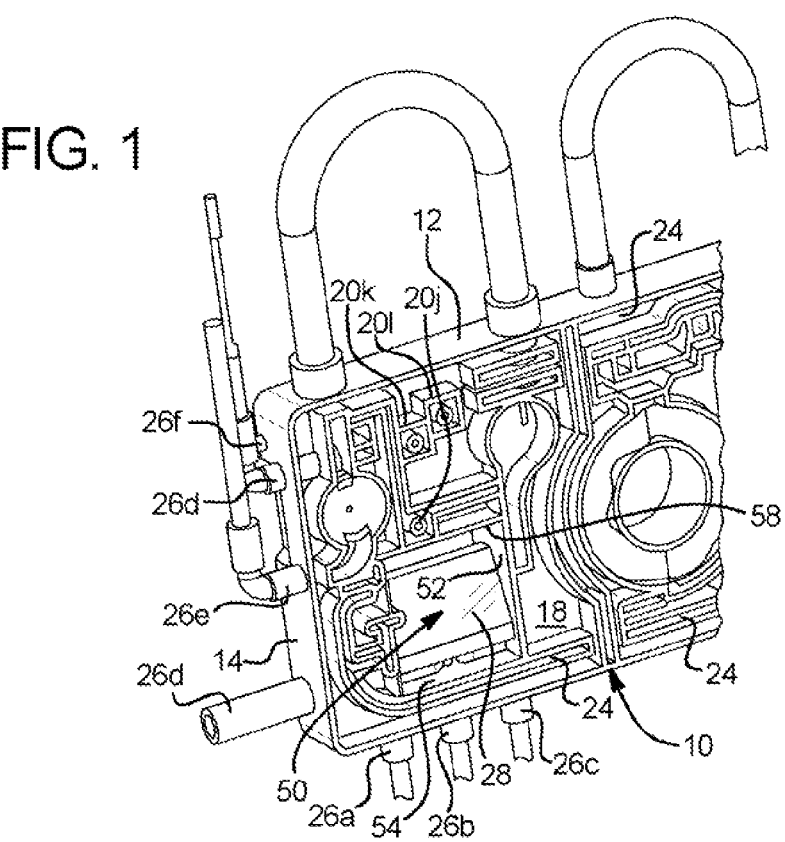
FIGS. 1 and 2 are perspective views of a disposable dialysis fluid cassette having one embodiment of a dialysis fluid air separation chamber of the present disclosure.
Figure 2:
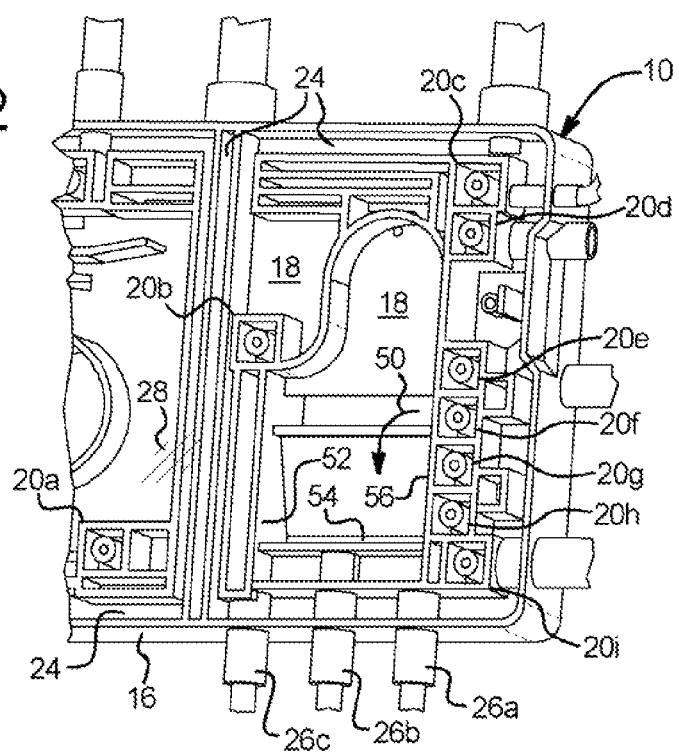

Referring now to the drawings and in particular to FIGS. 1 and 2, dialysis cassette 10 having air trap 50 illustrates one embodiment of the present disclosure. As discussed herein, air trap 50 refers generally to each of the air traps 50a to 50g discussed in detail below. Dialysis cassette 10 is operable with any type of dialysis instrument, such as a peritoneal dialysis instrument, hemodialysis, hemofiltration, hemodiafiltration or continuous renal replacement therapy instrument. Dialysis cassette 10 can hold a dialysis fluid, such as dialysate or blood. The dialysis fluid can be premixed or cassette 10 can carry a component of dialysate such as a dialysate concentrate.

Dialysis cassette 10 in one embodiment is part of a disposable set, which includes one or more supply bag, a drain bag, a heater bag, and tubing running from those bags (not illustrated) to dialysis cassette 10. Dialysis cassette 10 in one embodiment is disposable, however, dialysis cassette 10 could be cleaned for multiple uses in which case the air traps described herein are used multiple times. Dialysis cassette 10 includes a rigid portion have a cassette top wall 12, a cassette side wall 14 and a cassette bottom wall 16. Suitable materials for the rigid portion include polyvinyl chloride ("PVC"), acrylic, ABS, polycarbonate, and polyolefin blends. The rigid portion of cassette 10 also includes a base wall or mid-plane 18, which separates cassette 10 into first and second sides.

Cassette 10 on both sides of mid-plane 18 includes valve chambers 20a to 20l, which operate with a pneumatically and/or electromechanically operated valve actuator located in the dialysis instrument. Certain ones of the valve chambers, namely chamber 20k and 20l, operate as air separation chamber vent valve chambers. The air separation chamber may, or may not, have inlet and outlet valve chambers. The embodiment shown in FIG. 1 and FIG. 2 is intended to separate air from a flowing stream of blood and does not have either an inlet or an outlet valve chamber. Instead, pinch valves are intended to be used when it is necessary to close off the flow in the tubing coming from the patient (arterial line) and returning to the patient (venous line). Cassette 10 also includes peristaltic pumping tubes that operate with peristaltic pump actuators of the dialysis instrument. The cassette can alternatively include diaphragm pump chambers that operate with a pneumatically and/or electromechanically operated pump actuator.

Both sides of mid-plane 18 of cassette 10 include flow paths 24. It should be appreciated that cassette 10 can have different structural layouts without affecting the performance of air separation chamber 50. Air separation chamber 50 can be located on either side of mid-plane 18 for space purposes or for other reasons related to component layout.

In the illustrated embodiment, valve chambers 20a to 20l operate with a flexible cassette sheeting 28, which is welded, heat sealed or solvent bonded to rigid walls 12, 14, 16, air separation chamber walls, etc., of the rigid portion of cassette 10. Cassette sheeting 28 is also used as the pump diaphragm if a diaphragm pump is used instead of the peristaltic pump. Cassette sheeting 28 is also used to pump fluid through diaphragm when used. Suitable cassette sheeting 28 includes polyvinyl chloride ("PVC"), polypropylene/polyethylene blends, polypropylene or Kraton blends, polyester, polyolefin, and ULDPE. The suitable PVC sheeting can include, for example, monolayer PVC films, non-DEHP PVC monolayer films, monolayer non-PVC and multilayer non-PVC films (wherein different layers are chosen to provide strength, weldability, abrasion resistance and minimal "sticktion" to other materials such as rigid cassette materials). Multiple layers can be co-extruded or laminated with or without a gas barrier.

The dialysis instrument includes a controller unit that operates a program that controls when valve chambers 20a to 20l are open or closed. The controller unit can include, but is not limited to, a processor, memory, hardware (e.g. sensors, actuators, I/O boards, etc.), software, and algorithms. For example, inlet and outlet valve chambers 20k and 20l are open during dialysis fluid delivery and/or blood pumping to remove air from those fluids. Inlet valve chamber 20j is opened to delivery priming fluid directly into air separation chamber 50. Inlet valve chambers 20b and 20c are used to deliver priming fluid into the inlet and outlet of the peristaltic pump during priming and rinseback.

Inlet and outlet valves chambers 20e through 20i allow the system to direct the flow of fresh dialysate into the dialyzer secondary to perform hemodialysis or hemo-filtration, into the dialyzer primary inlet to perform pre-dilution hemo-filtration or into the dialyzer primary outlet to perform post-dilution hemofiltration. The independent control of the valves allows one disposable set and device to perform virtually any type of hemodialysis including hemo-diafiltration, CRRT, SCUF, etc.

The controller unit is also programmed to operate vent valve chambers 20k and 20l, so as to remove air from the air separation chamber in a manner so as not to affect the sterility of the dialysis fluid flowing through cassette 10. To this end, the controller unit can monitor the outputs from a single analog liquid level sensor, or multiple digital liquid level sensors, that are maintained in contact with the flexible film covering the domes shaped air collection portion of air separation chamber 50. When the liquid level sensors indicate that the liquid level has fallen, valve chambers 20k is first opened so that the pressurized air in air separation chamber 50 flows into the volume between valve chambers 20k and 20l. Valve 20k is then closed trapping the pressurized air. Valve 20l is then opened discharging the pressurized air. The controller unit is programmed to repeat the valve sequence for valve chambers 20k and 20l as required in order to maintain the desired liquid level in air separation chamber 50.

Cassette 10 in FIG. 1 also includes a plurality of rigid ports 26a to 26f extending from one of the walls, such as cassette top wall 12. Rigid port 26c draws the blood from the patient (arterial line) and rigid port 26b returns the dialyzed blood to the patient (venous line) Rigid ports 26e sends unprocessed blood to the dialyzer and rigid port 26a receives processed blood returning from the dialyzer. Rigid port 26d pulls spent dialysate (ultrafiltration) from the dialyzer and rigid port 26d delivers fresh dialysate to the dialyzer. Rigid ports 26d could alternatively be patient ports for performing PD. Port 26f is the saline or priming fluid port. The heparin port is not shown but is located midway between ports 26d and 26e.

Figure 4:
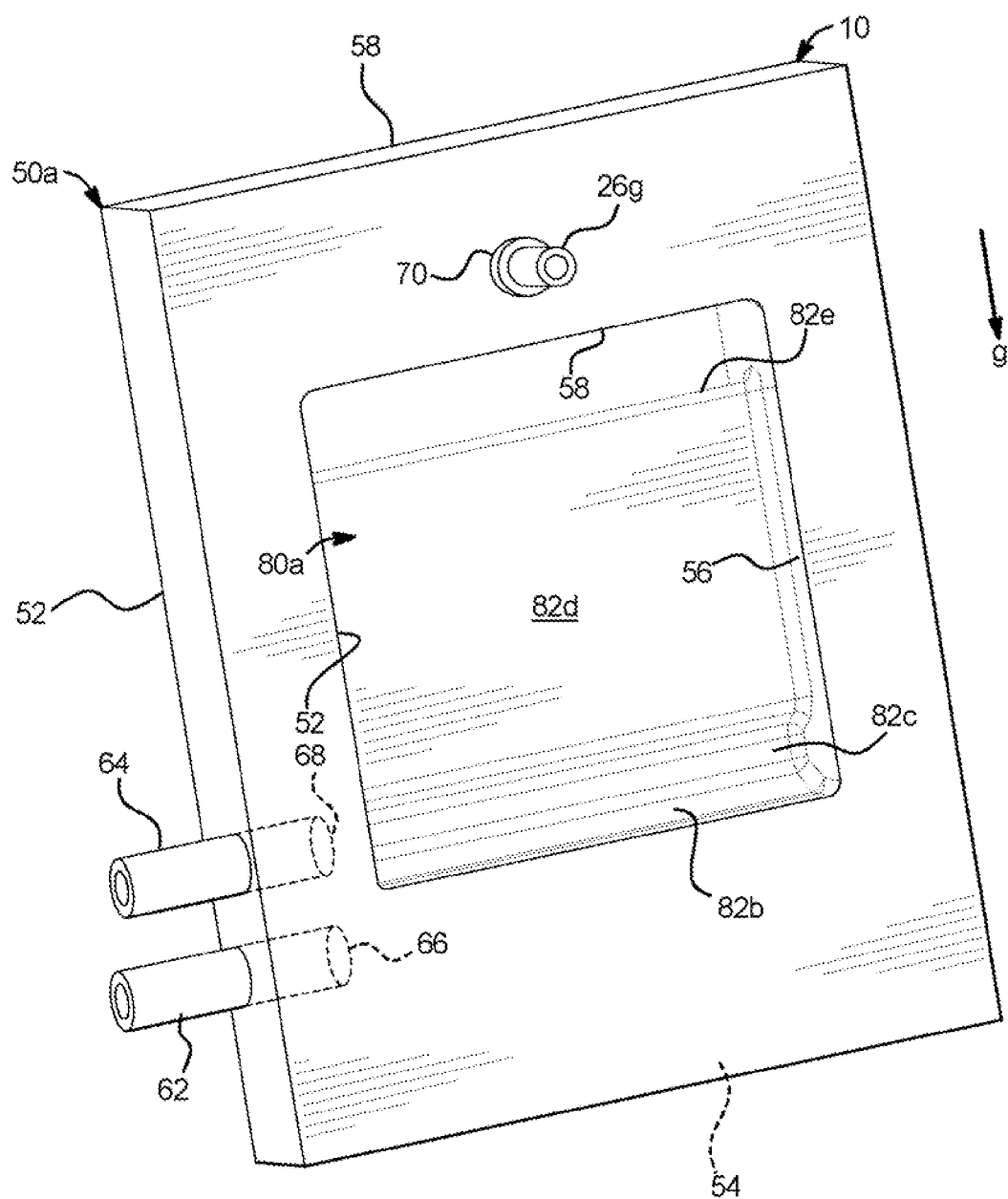

FIG. 4 illustrates a vent port 26g. Vent port 26g can vent air from air separation chamber 50 to atmosphere or to drain in different embodiments. Cassette 10 can include other apparatuses (not illustrated), such as pressure sensing areas, a heater flow path area (discussed below in connection with FIG. 13), and additional pumping areas, such as heparin and/or saline pumping areas (e.g., via diaphragm or peristaltic pump).

Figure 3:
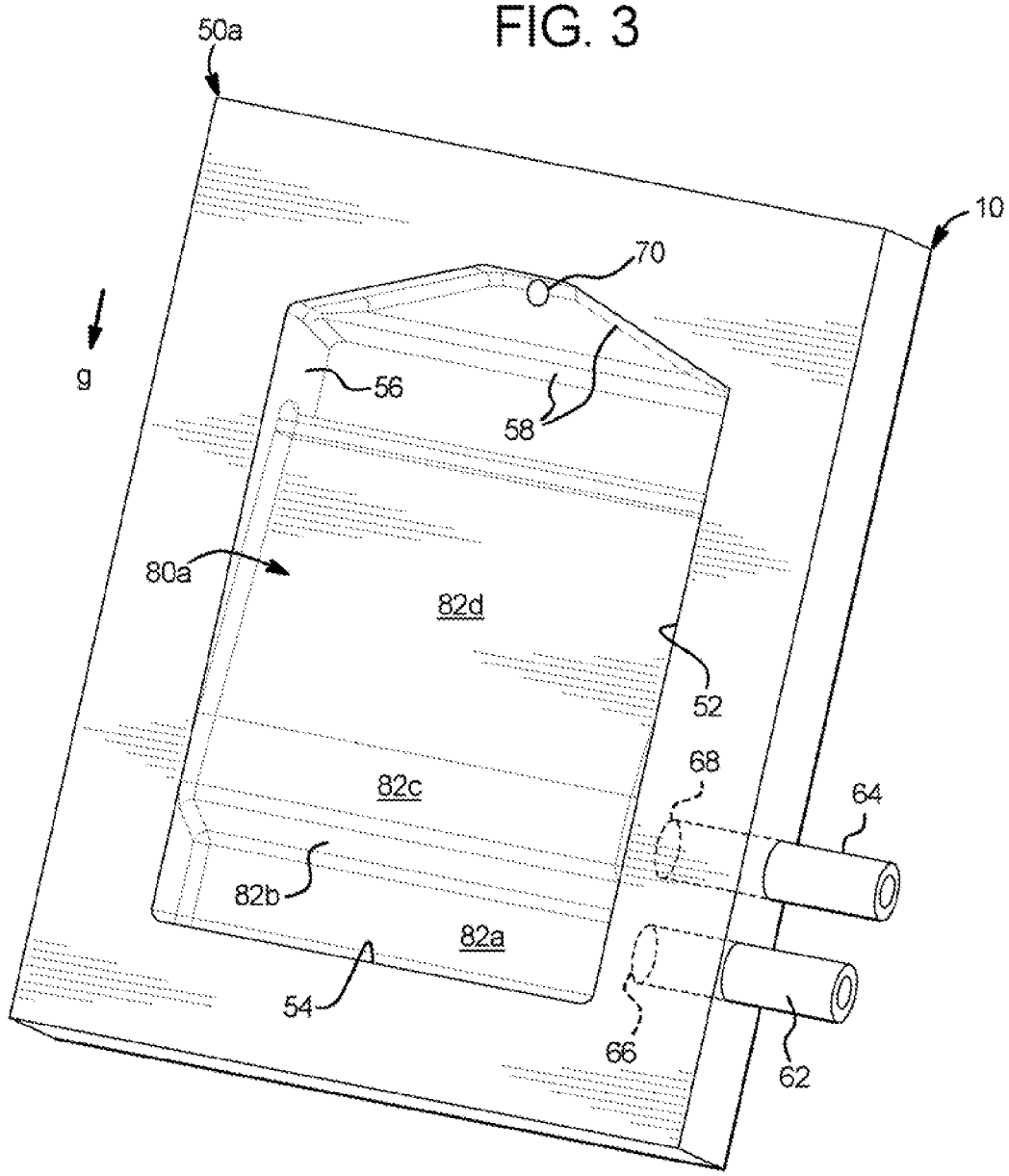
FIGS. 3 and 4 are perspective views showing the dialysis fluid air separation chamber of FIGS. 1 and 2 more closely.

FIGS. 3 and 4 show one embodiment of the air separation chamber or air trap of the present disclosure, namely, air separation chamber 50a. Air separation chamber 50a shows a portion of cassette 10 for reference, although it should be appreciated that air separation chamber 50a (and others discussed below) can be provided as a stand-alone component, e.g., housing 10 is a stand-alone unit. Here, the stand-alone can communicate fluidly with the disposable cassette via tubing.

Air separation chamber 50a includes a first side wall 52, a bottom wall 54, a second side wall 56 and a top wall 58. As seen in FIGS. 1 and 2, mid-plane 18 extends along the outside of walls 52 to 58 but not inside air separation 50, such that walls 52 to 58 extend the entire thickness of cassette 10. Here, both broad surfaces of air separation chamber 50 can be made of flexible sheeting 28, both can be made of rigid material, or one be made of rigid material while the other is made of flexible sheeting 28. For example, a piece of rigid material in the profile shape of air separation chamber 50a can be welded or solvent bonded to one or both sides of walls 52 to 58. Thereafter, the sheeting is welded or solvent bonded to the edges of the rigid broad side(s) of air separation chamber 50a to covert the remainder of cassette 10.

Inlet port 26b and outlet port 26a can be cassette flow paths as seen in FIGS. 1 and 2 or stand-alone flow passages 62 and 64 as shown in FIGS. 3 and 4. Inlet and outlet pathways 62 and 64 can be cassette flow paths as seen in FIGS. 1 and 2 or stand-alone flow passages as shown in FIGS. 3 and 4. In FIGS. 3 and 4, inlet pathway 62 and outlet pathway 64 communicate with air separation chamber 50 via inlet 66 and outlet 68, respectively, which are formed in first side wall 52 of air separation chamber 50. The inlet and/or outlet pathway communicates alternatively with air separation chamber 50 via an outlet 68 formed in second side wall 56 of air separation chamber 50 as illustrated in FIG. 9a.

The air separation chamber vent valves are not shown in FIG. 3 and FIG. 4. An external valve, or external valves, open and close a vent line connected to disposable cassette 10, which communicates with vent port 26g and with air separation chamber 50a via a vent outlet 70 seen in FIG. 3. External dual vent valve chambers, similar to 20k and 20l in FIGS. 1 and 2, allow the controller unit of the dialysis instrument to isolate a slug of air in the vent line before vent valve chamber 20l is opened, allowing the air to escape via vent port 26g to atmosphere or drain. In the programmed sequence, with vent valve chamber 20l closed, vent valve chamber 20k is opened allowing the vent line to become pressurized with air. Once the vent line becomes pressurized, valve chamber 20k is closed and valve chamber 20l is opened, relieving the pressure in the vent line.

With air separation chamber 50a, inlet pathway 62 and outlet pathway 64 are parallel to each other and are at least substantially perpendicular to the vent line. Side walls 52 and 56 are at least substantially orthogonal to walls 54 and 58, forming a square or rectangular air separation chamber 50a. FIG. 3 also shows the top 58 being tapered to smooth flow and prohibit air trapping. Likewise, bottom 54 can be tapered especially when the fluid inlet occurs on the bottom of the air separation chamber and impinges an upper plenum forming wall such as baffle portion 82b discussed below.

As seen in FIGS. 3 and 4, air separation chamber 50a includes a baffle 80a, which as illustrated includes a baffle portion 82a extending vertically upward from bottom wall 54 past inlet 62. A second baffle portion 82b jogs inwardly from baffle portion 82a, e.g., at a non-horizontal angle, into chamber 50a forming an inlet plenum. A third baffle portion 82c jogs upwardly from baffle portion 82b, e.g., vertically, extending past outlet 64. Wall 82d angles inwardly from baffle portion 82c, e.g., at a non-vertical angle, into chamber 50a, forming the bulk of baffle 80a.

Baffle 80a forces the flow of dialysis fluid vertically upward from inlet 62 and inlet plenum against the force of gravity g, along first baffle portion 82a of baffle 80a. Dialysis fluid hits baffle portion 82b and is forced to change direction. Dialysis fluid is then squeezed between baffle portion 82c and an outer surface (e.g., flexible sheeting) of the air separation chamber before extending vertically along primary baffle portion 82d, flowing over a free edge 82e of baffle portion 82d and down along baffle portion 82d into a plenum created by the back side of 82c and exiting air separation chamber 50a through exit opening 68 and outlet pathway 64.

The angle of baffle portion 82d causes the cross-sectional area of the dialysis fluid flow to increase and the fluid velocity to decrease as it rises up the inlet side of the baffle wall. The slowing of the dialysis fluid flow allows buoyancy forces more time to lift air bubbles from the dialysis fluid to an air collection portion of the air trap. As the fluid flow downward towards the outlet, the cross-sectional area of the dialysis fluid flow also increases and the fluid velocity decreases. This further increases the buoyancy force while decreasing the drag force.

Figure 5:
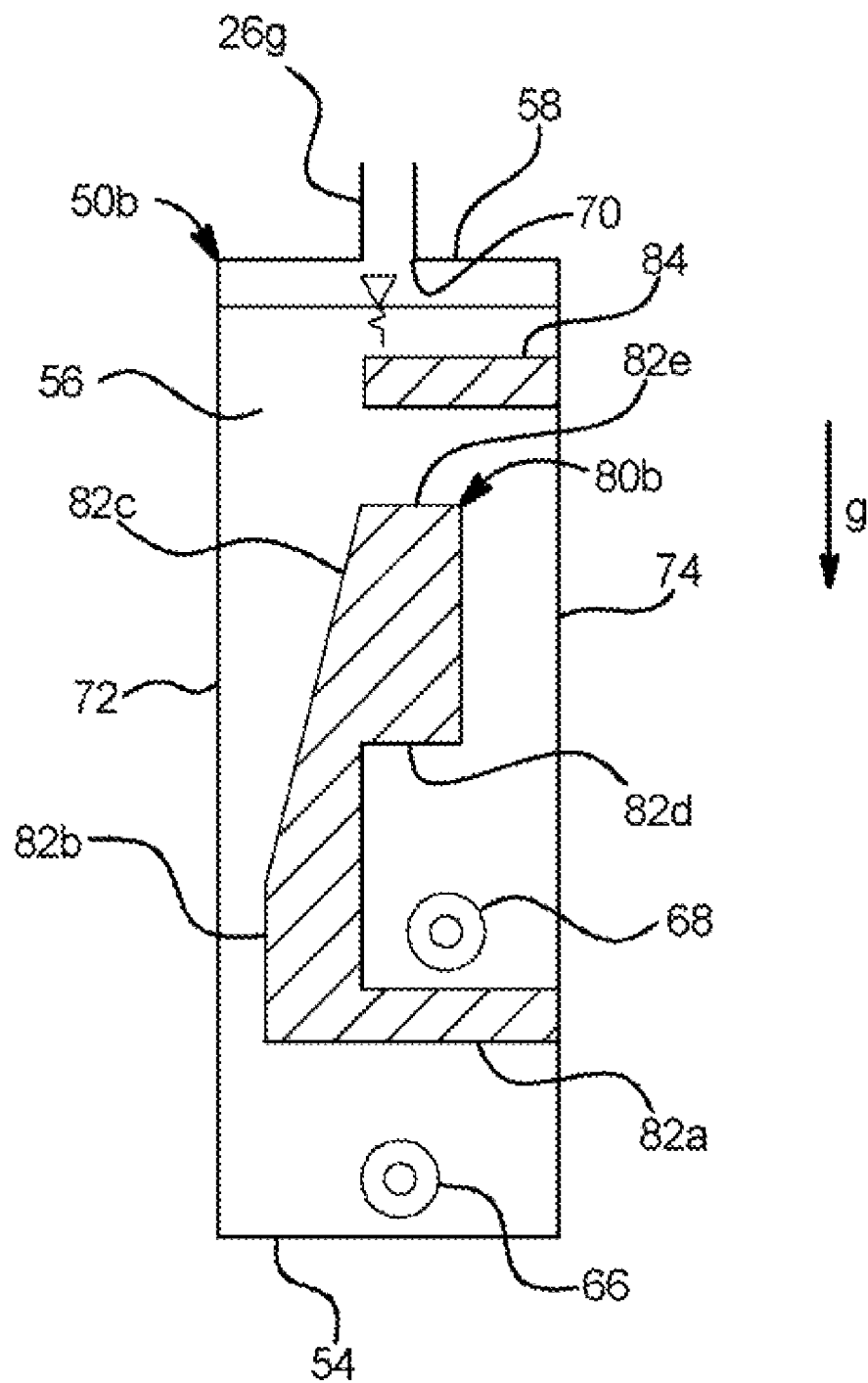
FIG. 5 is a sectioned elevation view of one embodiment of an air separation chamber of the present disclosure.

Referring now to FIG. 5, air separation chamber 50b operable with cassette 10 includes a different baffle or separation wall 80b. Here, as with chamber 50a, inlet 66 and outlet 68 are both formed in side wall 56, with inlet 66 located below outlet 68. Alternatively, one or both of inlet 66 and outlet 68 is/are formed in side wall 52 (not seen here). Vent opening 70 is located here in top wall 58 of air separation chamber 50b. Inlet 66, outlet 68 and vent opening 70 operate with cassette-based or stand-alone pathways as described above. Inlet 66, outlet 68 and vent opening 70 operate with associated valve chambers as described above.

As seen in FIG. 5, air separation chamber 50b includes a baffle 80b, which as illustrated includes a baffle portion 82a extending horizontally from side wall 56 to side wall 52. If either surface 72 or 74 of air separation chamber 50b is rigid, baffle portion 82a can be formed with or adhered to surface 72 and/or 74. If either surface 72 or 74 of air separation chamber 50b is made of flexible sheeting 28, the sheeting can be welded or bonded to baffle portion 82a. Baffle portion 82a forms an inlet plenum over inlet 66.

A second baffle portion 82b jogs upwardly from baffle portion 82a. A third baffle portion 82c extends upwardly from baffle portion 82b, clears outlet 68, and tapers inwardly from face 72, e.g., at an angle from vertical, into chamber 50a, forming the bulk of baffle 80b. A jog 82d on the outlet side of baffle 80b forms an outlet plenum for outlet 68.

Dialysis fluid hits horizontal baffle portion 82a of baffle wall 80b and is funneled towards face 72. Baffle portion 82b forces the flow of dialysis fluid vertically upward from inlet 62 and inlet plenum 82a against the force of gravity g, along second baffle portion 82b and squeezes the dialysis fluid between baffle portion 82b and face 72 (e.g., flexible sheeting) of the air separation chamber. Dialysis fluid then extends vertically along primary baffle wall 82c, flows over free edge 82e of baffle portion 82c and exits air separation chamber 50b through exit opening 68.

The taper of baffle portion 82c causes the cross-sectional area of the dialysis fluid flow to slow as it rises up the inlet side of baffle 80b. The slowing of the dialysis fluid flow allows buoyancy forces more time to lift air bubbles from the dialysis fluid to an air collection portion of the air trap.

Air separation chamber 50b also includes an upper baffle wall 84, which prevents fluid from exiting vent port 70 when air is vented from air separation chamber 50b. The bottom surface of baffle 84 is preferably angled upward so that air bubbles will tend to flow into the air accumulation chamber above baffle 84. FIG. 6 illustrates an output of a simulation of air separation chamber 50b of FIG. 5, showing pathways taken by one-hundred micron diameter air bubbles trapped within the dialysis fluid when flowing through air separation chamber 50b, calculated to have a 0.0005 micro-liter volume, wherein the dialysis fluid flowrate is about 500 ml/min and the pressure drop through the air trap is about 0.1 psi. Thus, the drag force of the rapidly flowing blood stream ($\mu$blood=3.62 cP and $\rho$blood=1.06 g/cc) will pull 100 micron diameter bubbles will flow through the air trap.

FIG. 7 illustrates an output of a simulation of air separation chamber 50b of FIG. 5, showing pathways taken by two-hundred-fifty micron diameter air bubbles trapped within the dialysis fluid when flowing into air separation chamber 50b, calculated to have a 0.008 micro-liter volume, wherein the dialysis fluid flowrate is about 500 ml/min and the pressure drop through the air trap is about 0.1 psi. Most of the 250 micron diameter air bubbles are to the top of the air separation chamber; however, some flow through the air trap.

Figure 8:
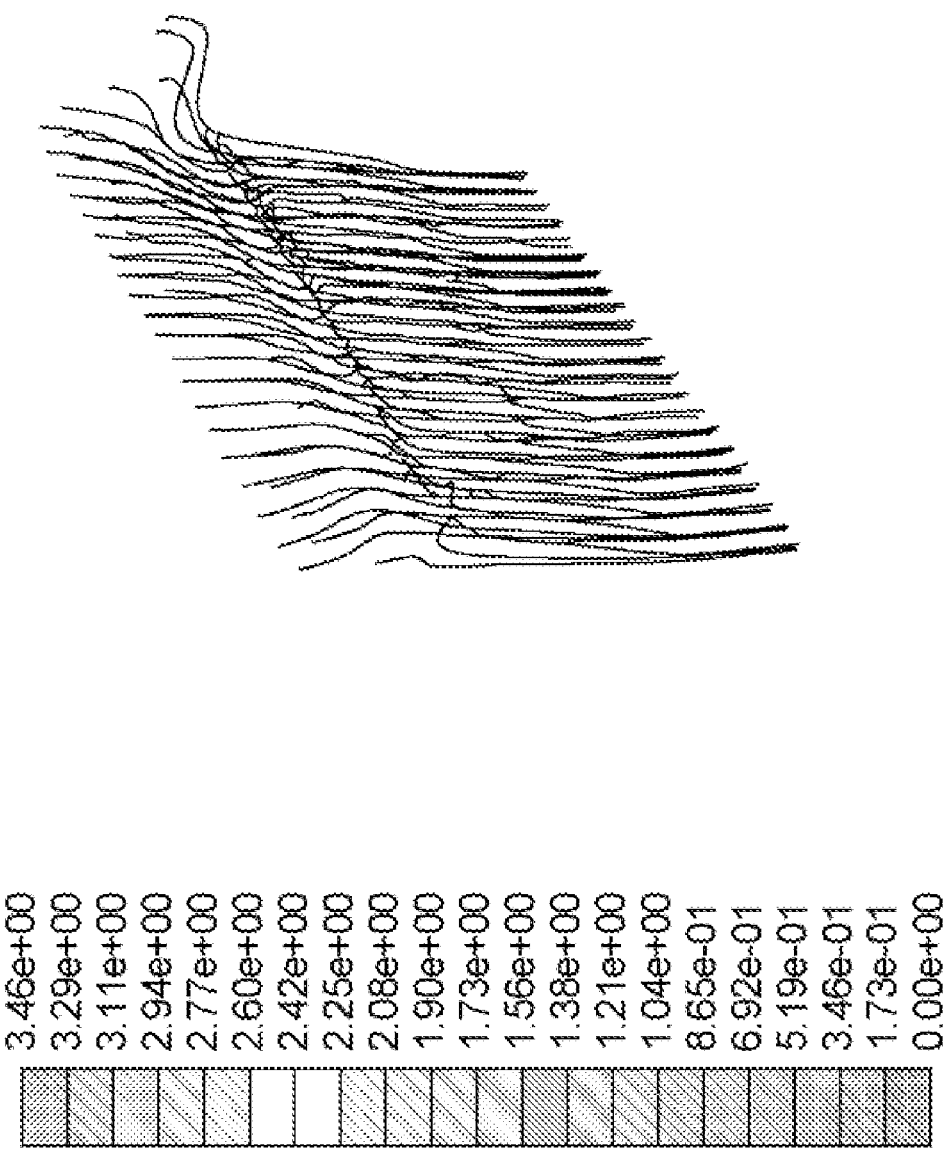

FIG. 8 illustrates an output of a simulation of air separation chamber 50b of FIG. 5, showing pathways taken by three-hundred micron diameter air bubbles trapped within the dialysis fluid when flowing through air separation chamber 50b, calculated to have a 0.014 micro-liter volume, wherein the dialysis fluid flowrate is about 500 ml/min and the pressure drop through the air trap is about 0.1 psi. All of the 300 micron diameter air bubbles float to the top of the air separation chamber. Thus, this air trap design, which is about 5 cm by 5 cm by 1.25 cm in size, can be expected to provide a significant margin between actual and required performance since our goal was to not pass air bubbles larger than 1 micro-liter in volume. The air bubble detector in the venous line is intended to detect and sum the volume of air bubbles larger than 1 micro-liter in volume that pass by it. An alarm will be posted and the therapy halted if this volume exceeds various thresholds per unit time. Our goal is to almost never encounter an alarm.

FIGS. 9A and 9B illustrate air separation chamber 50c, which includes alternative apparatus to the previous air separation chambers. Air separation chamber 50c includes inlet 66/pathway 62 and outlet 68/pathway 64 placed on opposite sides walls 52 and 56 of air separation chamber 50c. Inlet 66/pathway 62 and outlet 68/pathway 64 are located alternatively on the same side wall 52 or 56. Baffle 80c includes first and second baffle portions 82a and 82b, which are the same or very similar to that of air separation chamber 50b of FIG. 5. Baffle portion 82c is angled rather than tapered, however, providing more fluid volume per package size than air separation chamber 50b of FIG. 5. Baffle 80c includes an upper horizontal baffle portion 82d ending at free edge 82e, while forming an exit dialysis fluid plenum with outlet 68.

Baffle 80c further includes an integrated air vent valve chamber 90, including a valve chamber wall 92, valve port 94 and vent outlet 96 to vent channel 98. Face 74 or at least the portion of face 74 covering air vent valve chamber 90 is formed via flexible sheeting 28. When air vent valve chamber 90 is closed, air cannot pass through port 94, though outlet 96 to channel 98. When air vent valve chamber 90 is open, air can pass through port 94, though outlet 96 to channel 98. A valve chamber downstream from air vent valve 90 allows for the sealed release of air described above. Integral air vent valve chamber 90 saves space overall for cassette 10.

FIGS. 10A and 10B illustrate air separation chamber 50d, which includes alternative apparatus to the previous air separation chambers. Air separation chamber includes inlet 66/pathway 62 and outlet 68/pathway 64 placed on opposite sides walls 52 and 56 of air separation chamber 50d. Inlet 66/pathway 62 and outlet 68/pathway 64 are located alternatively on the same side wall 52 or 56. Here, however, inlet 66/pathway 62 is located above outlet 68/pathway 64. Baffle 80d further includes an integrated air vent valve chamber 90, including a valve chamber wall 92, valve port 94 and vent outlet 96 to vent channel 98.

Baffle 80d includes first and second baffle portions 82a and 82b, which are the same or very similar to that of air separation chambers 50b and 50c. Baffle portion 82c is angled more severely than baffle portion 82c of baffle 80c. Baffle 80d includes a second vertical baffle portion 82d and a second angled baffle portion 82e, ending at free edge 82f. Second angled portion 82e slows the velocity of dialysis fluid rising from inlet 66/pathway 62 and also slows the velocity of fluid returning along angled portion 82e towards baffle portion 82b to outlet 68/pathway 64. First angled portion 82c creates an inlet plenum around inlet 66/pathway 62.

Baffle 80e of air separation chamber 50e of FIGS. 11A and 11B is the same as baffle 80d of air separation chamber 50d of FIGS. 10A and 10B. The primary difference between air separation chamber 50e and air separation chamber 50d is the placement of inlet 66/pathway 62 and outlet 68/pathway 64, which are both vertically disposed and operable with bottom wall 54. The inlet plenum also has a second baffle 86, which provides a serpentine pathway through the inlet plenum. The serpentine pathway extends the length of the pathway and is intended to distribute the inlet flow as uniformly as possible over the length of the inlet plenum before it begin to pass vertically along separation wall 80e.

Cross-sectional area increases and slows the flow of dialysis fluid on the inlet and outlet sides of baffle 80e here via angled baffle portion 82c, while baffle portion 82e decreases cross-sectional area and speeds the flow in both cases. Vertical inlet 66/pathway 62 and outlet 68/pathway 64 can be switched from the position shown in FIGS. 11A and 11B.

Figure 12:
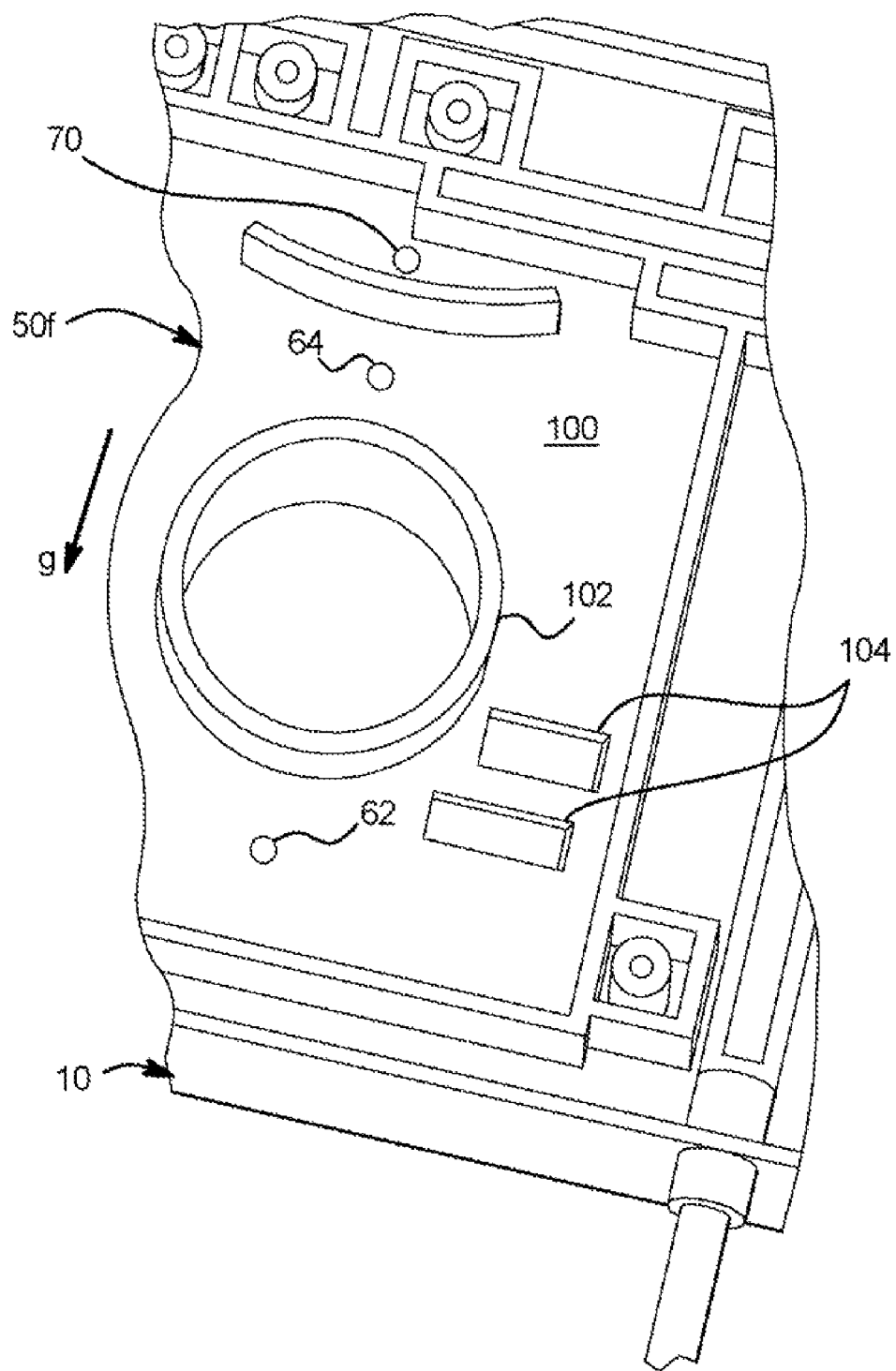
FIG. 12 is a perspective view of a disposable cassette and integral fluid heating/air separation chamber illustrating a further alternative embodiment for an air separation chamber of the present disclosure.

Referring now to FIG. 12, a further alternative air separation chamber 50f is illustrated. Here, the air separation chamber operates with a heating chamber 100. Heating chamber 100 includes a heating wall 102, which accepts heat from a heater element (not shown) such as a resistive or inductive heater element. As illustrated in FIG. 12, heating wall 102 has a substantially circular cross-section. Heating wall 102 transmits heat to fluid flowing within hybrid air separation chamber 50f/heating chamber 100, e.g., from inlet 62 to outlet 64. Baffles 104 are provided to increase heating contact time with wall 102 and to increase fluid mixing.

Baffles 104 also aid in allowing air to separate from the dialysis fluid as described herein. The baffles can be staggered and inclined to promote movement of air towards the top of air separation chamber 50f/heating chamber 100, where air outlet 70 is located. A splash wall is provided to prevent liquid from exiting through air outlet 70.

Figure 13:
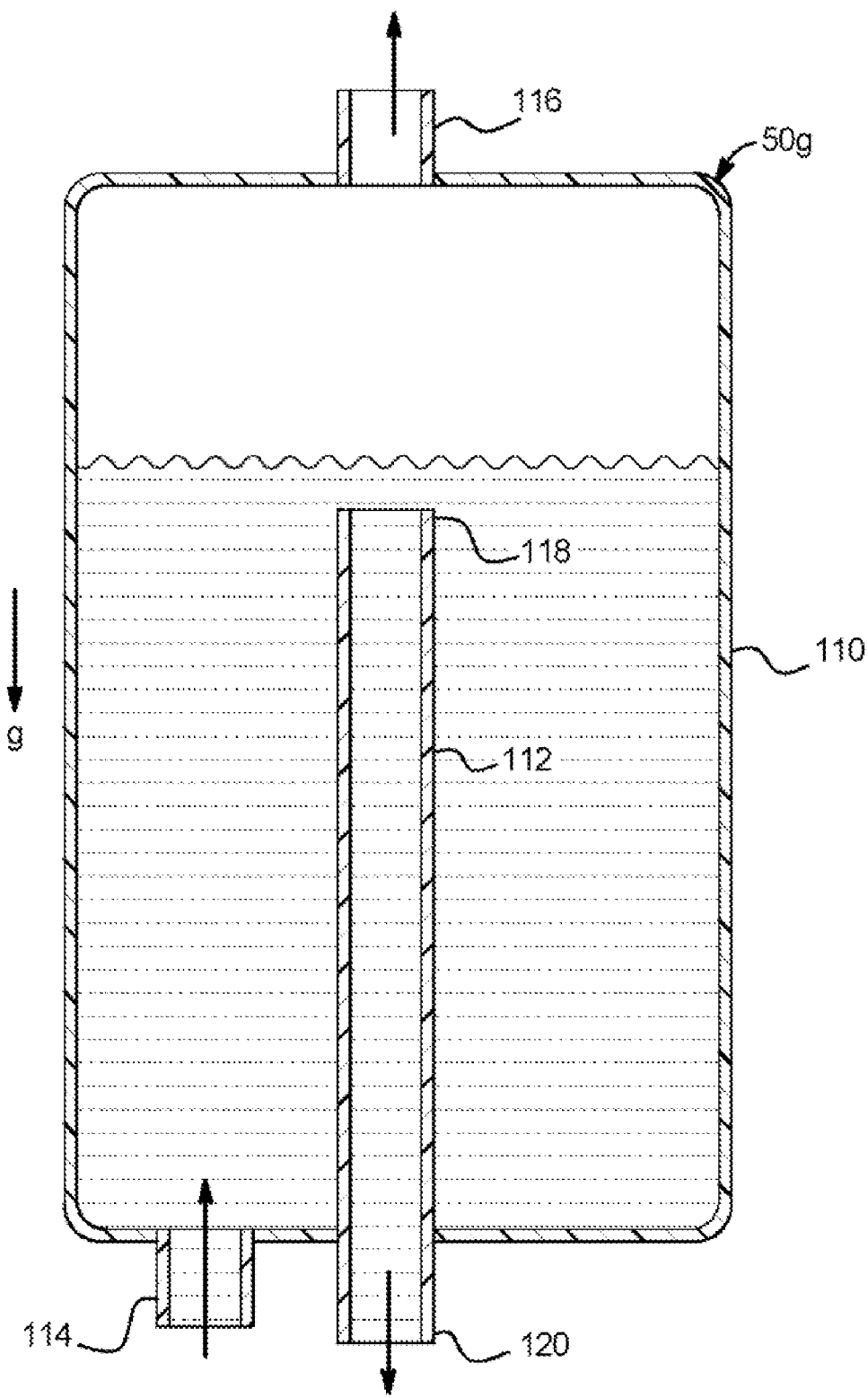
FIG. 13 is a sectioned elevation view of a concentric tube air separation chamber illustrating yet another alternative embodiment for an air separation chamber of the present disclosure.

Referring now to FIG. 13, yet another alternative air separation chamber 50g is illustrated. Here, the air separation chamber includes dual, e.g., concentric, tubes 110 and 112. Tubes 110 and 112 can have various shapes, for example, circular, rectangular, elliptical, or oval shape. Tubes 110 and 112 can be formed as part of cassette 10, fixed to cassette 10 or connected fluidly as a stand-alone device to cassette 10 via tubing connection. Tube 110 includes a dialysis fluid inlet 114 and an air vent outlet 116 as shown. Air vent outlet 116 can operate with multiple air vent valves as discussed above.

Inner tube 112 extends upwardly into outer tube 110 when air separation chamber 50g is mounted for operation. Fluid enters air separation chamber 50g from inlet 114, flows upwardly within outer tube 110, flows over a free end 118 of tube 112, flows down tube 112 and out dialysis fluid outlet 120. Although not illustrated, tube 110 can have baffles that increase the flow path within tube 110. Also not illustrated, tube 110 can have a splash plate that prevents fluid from exiting through air vent outlet 116.

Any of the air separation chambers discussed herein can operate with a mesh screen, e.g., in the two-hundred-fifty micron range to prevent particulates and clots from being returned to the patient. The mesh can also act as a nucleus for bubble formation when outgassing occurs. The mesh can be located at the fluid outlet of the air separation chamber or can extend across the top of the separation wall so that all flow must pass through it before entering the exit plenum.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A dialysis fluid cassette comprising:
 a rigid portion defining at least one valve chamber and a dialysis fluid pathway, the rigid portion including:
  a plurality of walls,
  a dialysis fluid inlet,
  a dialysis fluid outlet, and
  a separation wall extending from a first one of the plurality of walls to a second one of the plurality of walls, the separation wall having a free edge, the separation wall and the plurality of walls constructed and arranged so as to force dialysis fluid to flow from the dialysis fluid inlet around the free edge of the separation wall to the dialysis fluid outlet and to allow a cross-sectional area of the dialysis fluid pathway defined in part by the separation wall to increase as the dialysis fluid flows along the separation wall, to slow the flow of the dialysis fluid, allowing buoyancy forces to remove air from the dialysis fluid.

2. The dialysis fluid cassette of claim 1, wherein the separation wall is tapered to allow a cross-sectional area of a dialysis fluid pathway defined in part by the separation wall to increase as the dialysis fluid flows along the pathway, to slow the flow of dialysis fluid, allowing buoyancy forces to remove air from the dialysis fluid.

3. The dialysis fluid cassette of claim 1, the dialysis fluid inlet and outlet are disposed (i) each in first and second sidewalls of the plurality of walls; or (ii) in a bottom wall of the plurality of walls.

4. The dialysis fluid cassette of claim 1, the first and second ones of the plurality of walls being rigid and defining an air separation chamber, and which includes at least one flexible sheet fixed to the first and second ones of the plurality of walls, the at least one flexible sheet forming at least one of a first surface and a back surface of the air separation chamber.

5. The dialysis fluid cassette of claim 1, wherein the separation wall is tapered on an inlet side of the free edge of the separation wall.

6. The dialysis fluid cassette of claim 1, the separation wall angled such that the cross-sectional area of the dialysis fluid pathway increases as the dialysis fluid rises when the cassette is placed in a dialysis instrument.

7. The dialysis fluid cassette of claim 1, wherein the at least one valve chamber is in fluid communication with a vent opening.

8. The dialysis fluid cassette of claim 1, which includes a projection extending at least partially horizontally from the free edge of the separation wall, the projection narrowing the dialysis fluid pathway after the fluid flows around the free edge.

9. The dialysis fluid cassette of claim 1, the separation wall angled on an inlet side of the free edge of the separation wall.

10. The dialysis fluid cassette of claim 1, wherein the separation wall is bent at a plurality of different angles.

11. The dialysis fluid cassette of claim 1, the at least one valve chamber including a valve port operable with a piece of flexible sheeting attached to the cassette.

12. A dialysis fluid cassette comprising:
a plurality of walls defining at least one valve chamber, a dialysis fluid inlet, a dialysis fluid outlet and a dialysis fluid pathway; and
a baffle extending from a first one of the walls to an opposing second one of the walls, the baffle including an end fixed to a third one of the plurality of walls and a free end, the fixed end separating the dialysis fluid inlet from the dialysis fluid outlet, the baffle and the plurality of walls constructed and arranged such that the flow of dialysis fluid along the pathway defined in part by the baffle slows as the flow approaches the free end of the baffle.

13. A dialysis fluid cassette air separation method comprising:
providing a plurality of walls defining a dialysis fluid inlet, a dialysis fluid outlet and a dialysis fluid pathway;
providing a baffle extending from a first one of the walls to an opposing second one of the walls, the baffle including an end fixed to a third one of the plurality of walls and a free end; and
flowing dialysis fluid along the dialysis fluid pathway past a free end of the baffle such that the flow of dialysis fluid along the pathway defined in part by the baffle slows as the flow approaches the free end of the baffle.

14. The dialysis fluid cassette air separation method of claim 13, wherein the baffle is tapered to allow a cross-sectional area of a dialysis fluid pathway defined in part by the separation wall to increase as the dialysis fluid flows along the pathway, to slow the flow of dialysis fluid, allowing buoyancy forces to remove air from the dialysis fluid.

15. The dialysis fluid cassette air separation method of claim 13, wherein the baffle is angled to allow a cross-sectional area of a dialysis fluid pathway defined in part by the separation wall to increase as the dialysis fluid flows along the pathway, to slow the flow of dialysis fluid, allowing buoyancy forces to remove air from the dialysis fluid.

* * * * *